(12) United States Patent
Hall et al.

(10) Patent No.: US 6,911,026 B1
(45) Date of Patent: Jun. 28, 2005

(54) MAGNETICALLY GUIDED ATHERECTOMY

(75) Inventors: Andrew F. Hall, St. Charles, MO (US); Jonathan C. Sell, Eagan, MN (US)

(73) Assignee: Stereotaxis, Inc., St. Louis, MO (US)

( * ) Notice: Subject to any disclaimer, the term of this patent is extended or adjusted under 35 U.S.C. 154(b) by 439 days.

(21) Appl. No.: 09/352,161

(22) Filed: Jul. 12, 1999

(51) Int. Cl.[7] .............................................. A61B 17/22
(52) U.S. Cl. ............................ 606/28; 606/45; 606/48; 606/159; 128/899
(58) Field of Search ............................... 606/159, 6–10, 606/11–18, 27, 28, 45, 48; 128/653.1, 660.03, 899

(56) References Cited

U.S. PATENT DOCUMENTS

| 4,244,362 A | 1/1981 | Anderson |
| 4,671,287 A | 6/1987 | Fiddian-Green |
| 5,464,023 A | 11/1995 | Viera |
| 5,592,939 A * | 1/1997 | Martinelli ................. 128/653.1 |
| 5,623,943 A | 4/1997 | Hackett et al. |
| 5,630,427 A | 5/1997 | Hastings |
| 5,636,644 A | 6/1997 | Hart et al. |
| 5,647,843 A | 7/1997 | Mesrobian et al. |
| 5,706,827 A | 1/1998 | Ehr et al. |
| 5,769,843 A * | 6/1998 | Abela et al. ................... 606/10 |
| 5,904,147 A * | 5/1999 | Conlan et al. .............. 128/899 |

* cited by examiner

*Primary Examiner*—Michael H. Thaler
(74) *Attorney, Agent, or Firm*—Harness, Dickey & Pierce, P.L.C.

(57) ABSTRACT

Atherectomy devices are guided by and manipulated by externally applied magnetic fields to treat total or partial occlusions of a patient's vasculature.

26 Claims, 7 Drawing Sheets

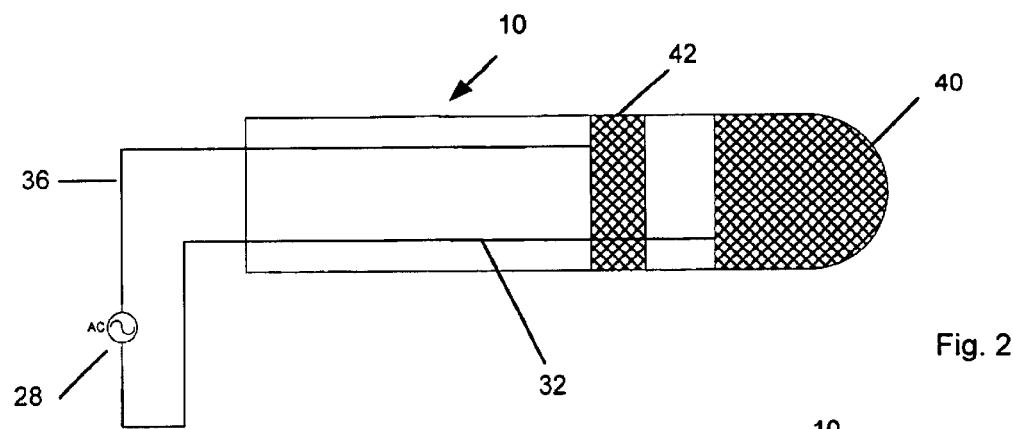
Fig. 2
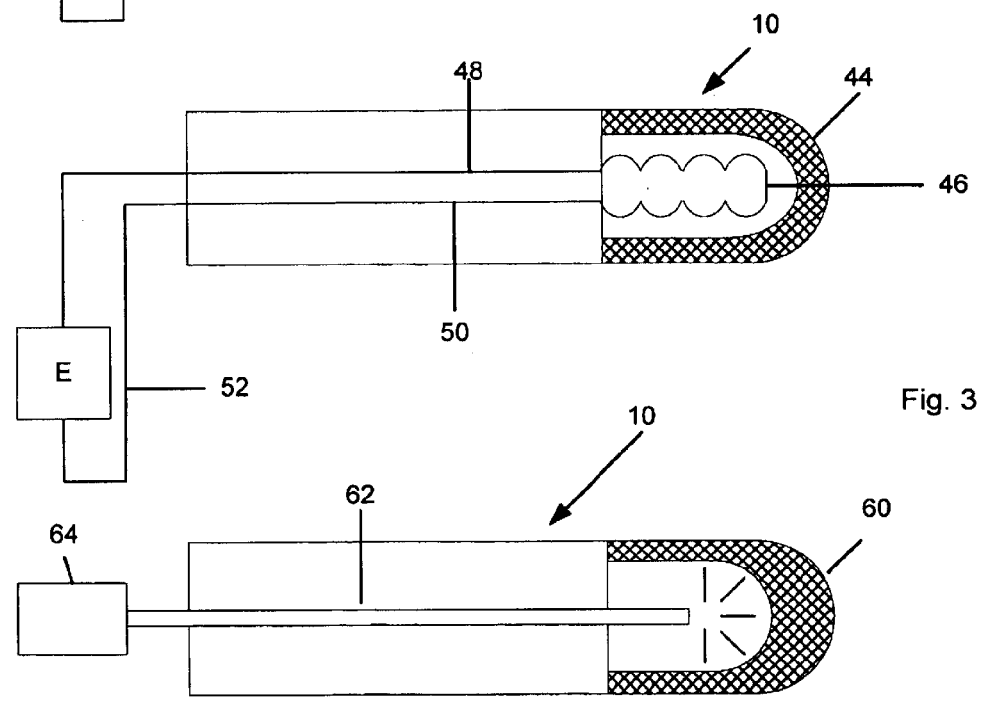
Fig. 3
Fig. 4

MAGNETICALLY GUIDED ATHERECTOMY

CROSS REFERENCE TO RELATED CASES

This application is a continuation-in-part of U.S. patent application Ser. No. 09/281,241, filed Mar. 30, 1999, the disclosure of all of which is incorporated by reference.

FIELD OF THE INVENTION

The present invention relates generally to the removal of occlusive material from body lumens, and more particularly both methods and devices for magnetically guided atherectomy of totally occluded arterial vasculature. Catheters which employ thermal as well as other energy sources are disclosed along with complementary equipment for carrying out the procedures.

DESCRIPTION OF THE PRIOR ART

Arteriolosclerosis is a progressive disease marked by deposits within the lumen of arterial vessels. Removal of these deposits restores blood flow and is a preferred treatment for this disease. In instances where the vessel cannot be salvaged, bypass grafts may be used to treat the disorder.

A wide range of recannalization techniques have been developed over time. The primary technique in clinical use today is balloon angioplasty. This is a "mechanical" treatment where a balloon at the treatment site is inflated to compress obstructive material against the vessel wall. In most treatment protocols the recannalization device is navigated to the treatment site through the patent's vasculature. The so called "Seldinger" technique is used most often to gain access to and navigate through the blood vessels. In this technique the catheter enters the body in the groin area and is moved through the vasculature to the heart with the assistance of both guidewire and occasionally guide catheters or sheaths.

Although balloon angioplasty is probably the most common procedure, there are several drawbacks to this type of device. One problem is that the vascular occlusion must first be crossed with a guide wire to position the balloon. The balloon device follows the guide wire thorough the lesion and the wire biases the balloon against the walls of the vessel. If the vessel is totally occluded the wire cannot cross the lesion and therefore cannot be used to guide the balloon.

Other energy sources for recannalization have been proposed and studied as well. For example, U.S. Pat. No. 5,318,014 to Carter, teaches a device to treat occlusions with ultrasound. The Drasler U.S. Pat. No. 5,370,609 teaches the use of a high-energy rearward facing water jet to remove occlusive material. The art teaches the use of rotating mechanical burrs or blades for removing material. See for example Pannek U.S. Pat. No. 5,224,945. Also the use of heat to reform and remodel a vessel is know from Eggers U.S. Pat. No. 4,998,933 among others.

SUMMARY

The atherectomy devices according to the invention include a magnetic element that allows for the remote manipulation of the distal end of working tip of the catheter by a magnetic surgery system (MSS) or other magnetic field generator operated outside of the patient.

The application of external fields and gradients allows the physician to control the orientation and location of the distal tip of the catheter in the vessel at the treatment site. This permits the use of small and potentially single size catheters to treat either partial or total occlusions in the vasculature.

In operation the device is moved to various treatment sites or locations in a vessel under the guidance of the MSS. The methods of the invention may be partially automated in the sense that the physician can image the current location of the device and program a desired location with the MSS and designate a location or orientation of the device in a vessel. The MSS system can provide feedback to the physician to help the physician direct the device as "planned" with the MSS workstation. Robotic control of the device is also contemplated wherein the motion of the device in the vessel is entirely under software control. In this instance physician observation and transducer feedback manages the procedure.

Any of a variety of energy sources can be used to carry out the recannalization process of the invention, although thermal energy is preferred and is used as an illustrative but limiting energy source. The source of heat may include optical or radio frequency energy sources. However, the device is also useful with hydraulic energy, direct laser sources or ultrasonic energy sources. Physician supplied energy is contemplated as well in the sense that a doddering wire may manipulated by the physician and guided magnetically to treat the occlusion.

Devices which rely on heat or which generate heat in the body may include fluid cooling to manage the distribution of heat. Several device with adjunctive fluid delivery are shown as illustrative of the invention.

Additional "delivery" structures are present in some embodiments of the device and may be used to accommodate various medical techniques and methods. For example lumens for "over the wire" and "rapid exchange" delivery of the catheters are shown. Also these lumens may be used with imaging and localization devices to carry out the methods of the invention. These lumens may also be used to introduce contrast agent into the treatment site.

Localization structures are disclosed for use in the procedure. Preoperative Magnetic Resonance Imaging (MRI), Computed Tomography (CT) or Ultrasound scans provide a "roadmap" for the procedure while X-ray, Doppler ultrasound, or other localization techniques are used to display the current real time position of the device in the lumen.

It is also contemplated that the "open" lumens of the device can be used with ultrasonic or laser based imaging systems to characterize the nature of the occlusion.

BRIEF DESCRIPTION OF THE DRAWINGS

Throughout the various figures of the drawing like reference enumerates refer to identical structure. A typical and exemplary set of embodiments of the invention are shown in the drawing but various changes to the devices may be made without departing from the scope of the invention wherein:

FIG. 2 is a schematic diagram of a bipolar thermal catheter;

FIG. 3 is a schematic diagram of a resistance heated thermal catheter;

FIG. 4 is a schematic of a laser-heated catheter;

DETAILED DESCRIPTION THE INVENTION

Figure 1:
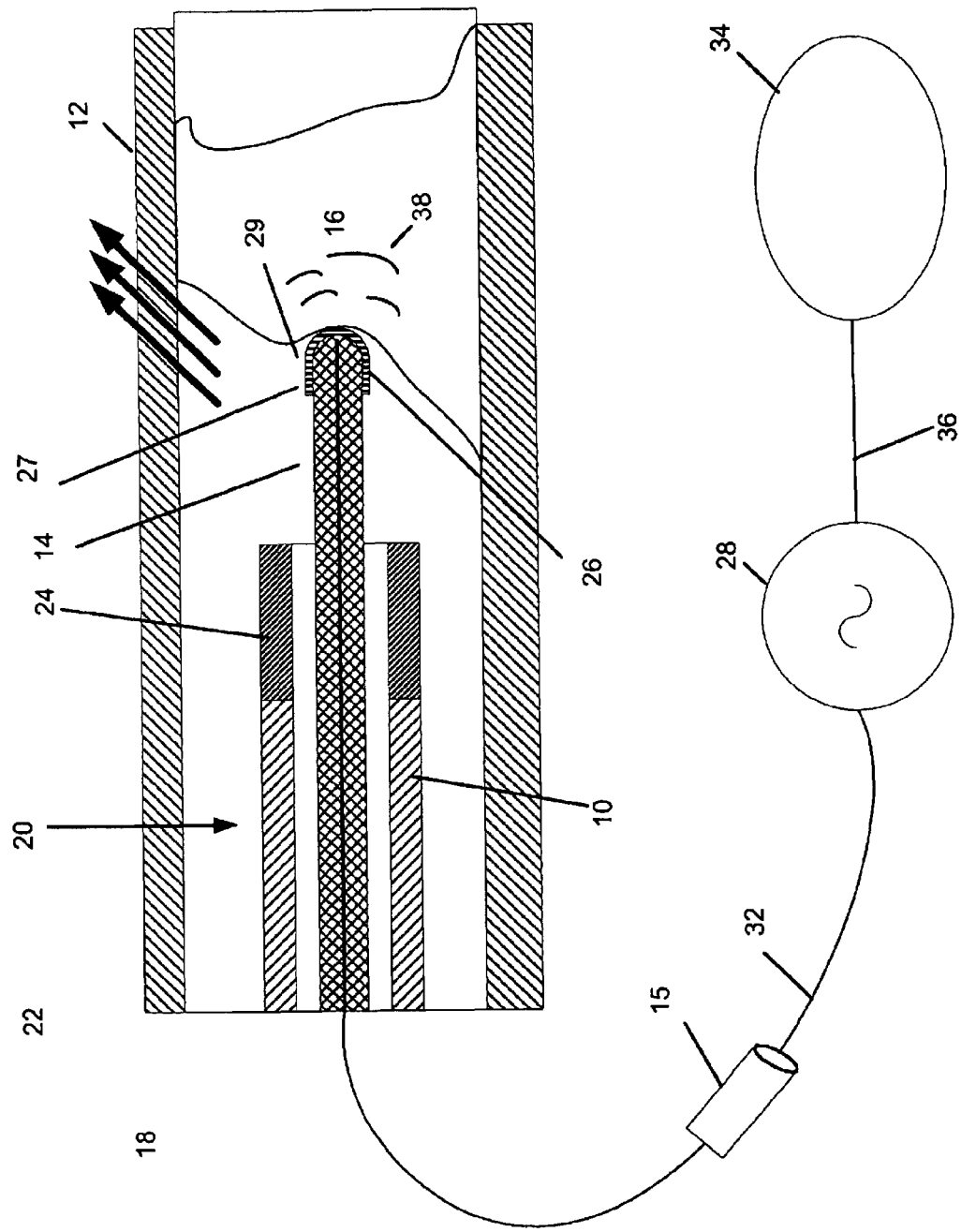
FIG. 1 is schematic diagram of a thermal catheter in a vessel.

FIG. 1 shows a thermal catheter 10 in a vessel 12. The distal tip section 14 of the device is shown in a vessel while the proximal section 15 is illustrated as a fragment located outside of the vessel 12. In general, the construction of the proximal end of the device and configuration and power couplings are within the ordinary skill of this art and are illustrated schematically in FIG. 1. For clarity the detailed disclosure is directed to the distal tip structures. However it should be recognized that the devices are intended for use in coronary vessels, the overall length of devices in accordance with this invention are 30 or more inches long and typical are between 2 and 12 French in diameter. It should be understood that coronary use is merely illustrative and other vessels and body lumens may be addressed therapeutically using the invention. The proximal end will carry suitable hubs and connections for the wires and lumens discussed in connection with the distal tip.

In FIG. 1 the distal tip 14 of the catheter 10 abuts a total occlusion 16. A guidewire 18 shown in phantom, and sheath 20 may be used together to deliver the catheter 10 to the treatment site near the occlusion 16. Either or both of the guidewire or sheath may have a magnetic element 22 included in its design to assist in access to the treatment site. For instance the guide wire 18 may have a magnet 22 located at its distal tip. Similarly the sheath may have a magnetic tube 24 located at its distal tip. However, for the purposes of this disclosure the magnetic elements on the guide wire or sheath permit the applied field or gradient to orient the distal tip. In FIG. 1 the forces generated on the tip by an external magnet are shown by vectors indicated by reference numeral 9. The physician can advance the guidewire or sheath by pushing on the proximal end of the device with the distal tip direction determined in part by the magnetic forces represented at 9. The magnetic orientation of the tip coupled with physical motion applied to the proximal end of the device positions the device. The physical motion can be supplied by either the physician or a robotic element.

The thermal catheter embodiment of FIG. 1 has a heated tip 26. Preferably this tip is formed from Hiperco or other magnetically active metallic material. In this context iron containing alloys of steel which are attracted to magnets are suitable choices for the tip material. Although the distal tips show are shown as hemispheric in shape for consistency of explanation it should be understood that other forms and shapes are operable so the shape should be understood as illustrative and not limiting. In use heat is delivered by the tip 26. The lines located by reference numeral 38 represent heat transfer to the occlusion 16, which allows the tip 26 to move through the occlusion 16. In this embodiment the tip 26 is heated with RF energy from an RF source 28. The RF source is coupled to the tip by a wire 32. A patch electrode 34 having a large area may be placed on the patient to complete the circuit to the RF source 28 through wire 36. This configuration may be called "monopolar" in contrast to the "bipolar" configuration shown in FIG. 2. A coating 27 may be applied to the surface of the distal tip to prevent sticking or adhesions. The coating 27 may also increase biocompatibility or improve heat transfer through the device. Both polymeric materials such as Teflon and metallic materials such as titanium nickel alloy are suitable for this application. Therefore the illustrative embodiments of the invention should be considered to be "composite" constructions where individual elements may be made of more than one material as indicated by coating 29.

FIG. 2 shows a distal tip embodiment for a thermal catheter 10, which includes two metal structures that are insulated from each other. The first structure is the distal tip 40 which is metal and may be magnetically active. The wire 32 couples this tip to the RF source 28. The second element is the return electrode 42. Preferably this function is served by metallic ring or band 42 which is coupled to the RF source 28 through the wire 36. In this embodiment one or both of the metallic elements may be magnetically active. Also partial rings which surround only part of the catheter are contemplated within the scope of the invention although they are not preferred. In general the exact shape of the distal rings will not be critical to the operation of the invention.

FIG. 3 shows a resistance heated embodiment of a thermal catheter 10 where the distal tip 44 is magnetically active metal. The tip 44 is electrically isolated from, but in thermal contact with the resistance wire heater 46 located near the tip. Wire 48 and wire 50 couple the heater 46 to the electrical power source 52 which may be an AC or DC source which may be modulated to control the energy delivery to the tip.

Figure 5:
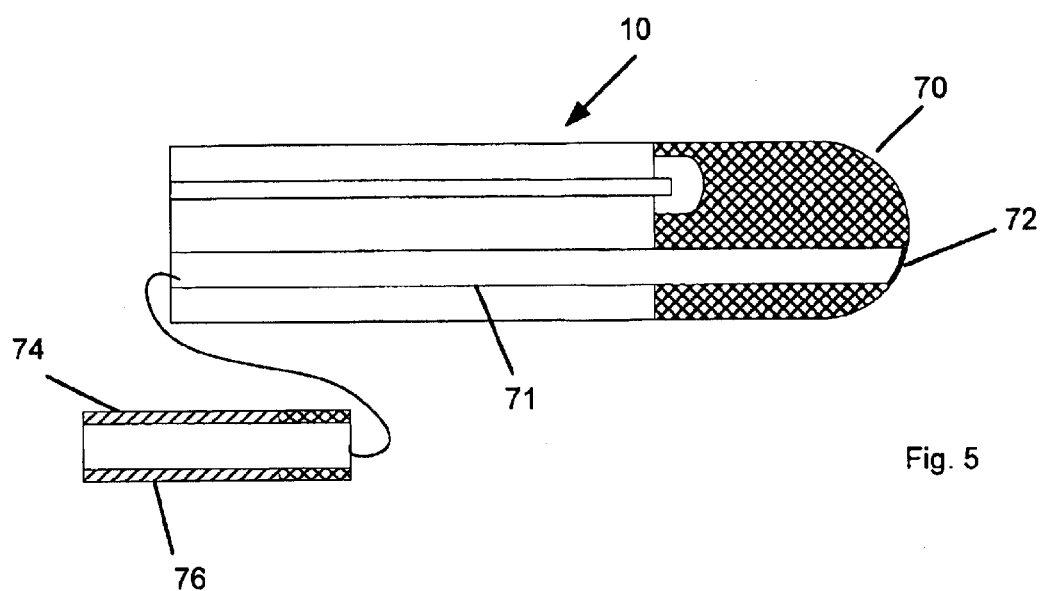
FIG. 5 is a schematic of a thermal catheter having an additional lumen.

FIG. 4 shows a laser heated embodiment of the thermal catheter device 10. In this embodiment the tip 60 absorbs radiation from the optical wave guide 62 coupled to the laser source 64. In operation the laser energy source may operate continuously or intermittently to deliver energy to the tip 60. In operation the laser light impinges on the tip structure and it is absorbed and converted to heat. The distal tip 60 may be magnetic or may be made from a magnetically active material. In general, and depending on detail design issues the surface of the tip may or may not be electrically conductive. In this particular embodiment it should be clear that the thermal requirements of the tip are significant in contrast to other embodiments where electrical conductivity is critical. It is contemplated that the distal tip may be made of ceramic or "glassy" material FIG. 5 shows an embodiment of the invention wherein thermal catheter 10 has a distal tip 70 which has a tube 71 that has an open lumen 72 which communicates to the proximal end of the device. This lumen 72 can be used for several purposes. For example, the lumen can accommodate either an imaging wire 76, ultrasonic or laser imaging, or a guide wire 74. In operation the preferred ultrasonic imaging wire can be used to visualize and locate the occlusion. Once the occlusion has been located and characterized, the correct amount of power can be delivered to the distal tip 70. Typically the ultrasound imaging wire would be withdrawn and parked in the lumen 72 proximally to prevent heat damage to the transducer of the imaging wire. During device placement the lumen can be used with the guidewire 74 to access the treatment site.

The lumen can also be used with an optical fiber to perform laser induced florescence spectroscopy or optical low coherence reflectometry. These procedures can be used to "look at" and evaluate the obstruction during treatment.

Figure 6:
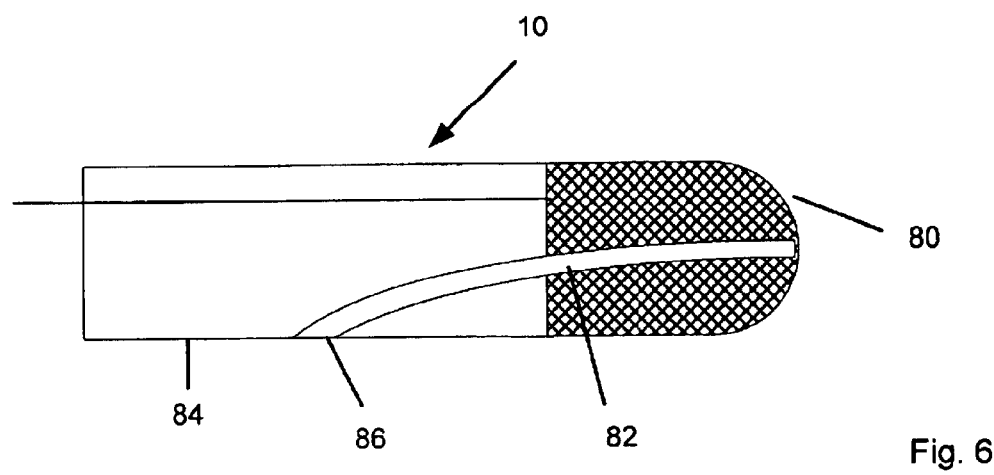
FIG. 6 is a RF heated catheter with a rapid exchange lumen.

FIG. 6 is an example of a "rapid exchange" delivery configuration for the thermal catheter 10. The distal tip 80 as an open lumen 82 which is relatively short and exits the side of the catheter body 84 at a location distal of the proximal end of the device 10. This opening can receive a guide wire which can be used to position the device near the occlusion.

Figure 7:
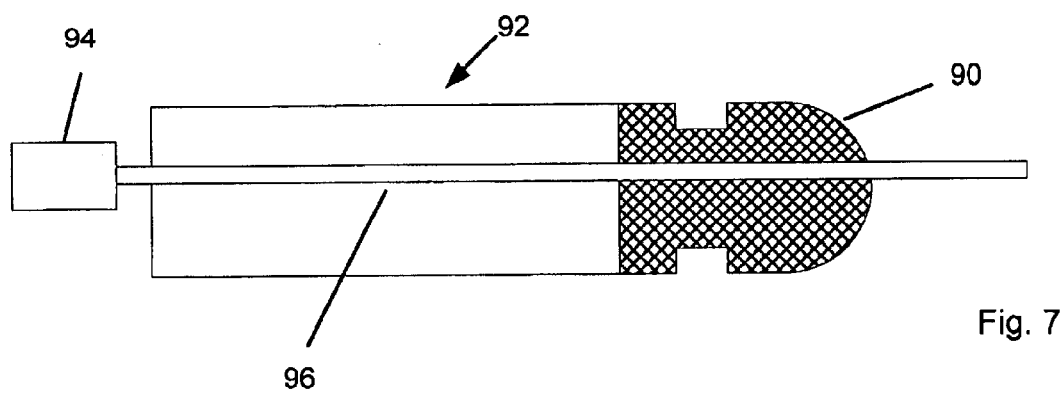
FIG. 7 is a an ultrasound atherectomy device driven by an external horn.

FIG. 7 represents an ultrasound energy source catheter 92. The ultrasonic horn 94 is coupled to the waveguide 96 which in turn terminates in a distal tip 90. The waveguide may extend beyond the tip. In operation the delivery of ultrasound energy to the distal tip results in the formation of very small bubbles which dislodge the nearby plaque or other obstructing material. In this embodiment the distal tip 90 may be formed of Hiperco or other magnetically active material.

Figure 8:
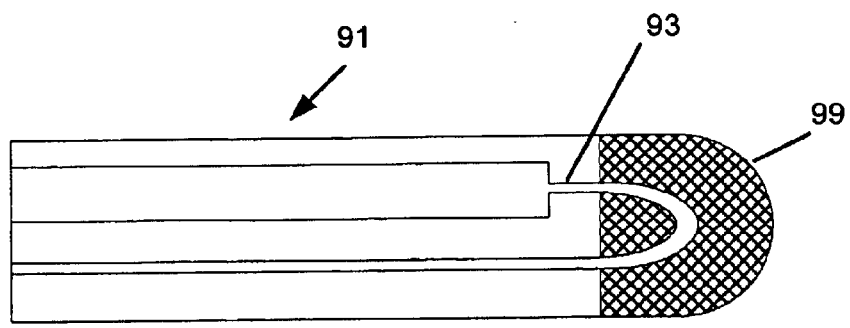
FIG. 8 is a hydraulic catheter.

FIG. 8 represents a hydraulic catheter 91 which uses the force of a jet of fluid emerging from nozzle 93 to disrupt the occlusive material. In this device the distal tip 100 may be made from Hiperco or another magnetically active material.

Figure 9:
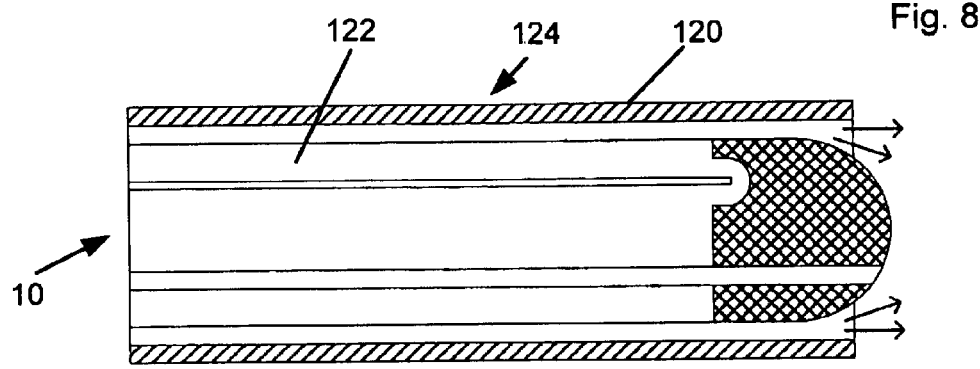
FIG. 9 is a an optically heated catheter in a sheath.

FIG. 9 shows the device 10 of FIG. 5 located in a sheath 120. The space between the sheath and the catheter body 122 can be flooded with contrast agent to reveal the location of the catheter with respect to the to the occlusion. At some power levels the space can be used to conduct cooling fluid to the tip to help regulate the temperature and temperature distribution of the device 124. Saline injection can also be used to prevent implosion of vapors in the blood at the treatment site.

Figure 10:
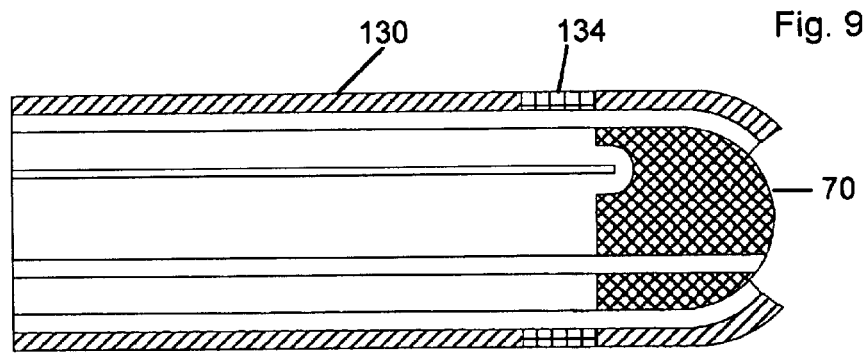
FIG. 10 is a an optically heated device with an auxiliary lumen.

FIG. 10 shows the device 78 of FIG. 5 in a sheath that limits the movement of the distal tip 70. In this version of the device the sheath 130 positions the distal tip 70 near the guide magnets 134. This allows the physician to move the tip with the MSS and to control the exit of fluid from the sheath.

Figure 11:
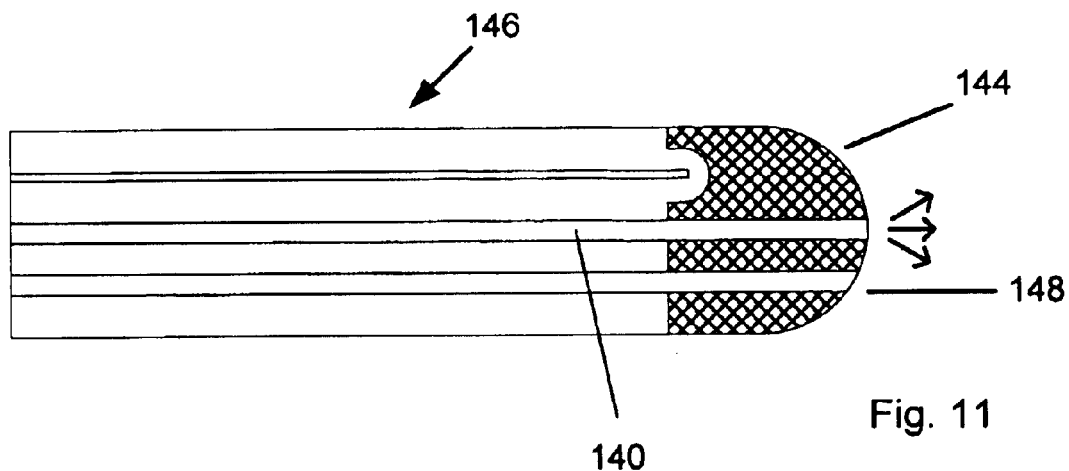
FIG. 11 is a an optically heated device with multiple lumens.

FIG. 11 represents a multilumen construction where a fluid supply lumen 140 is provided to irrigate the tip 144 of the catheter 146. An offset guide wire lumen 148 is provided for used with imaging and locating devices.

Figure 12:
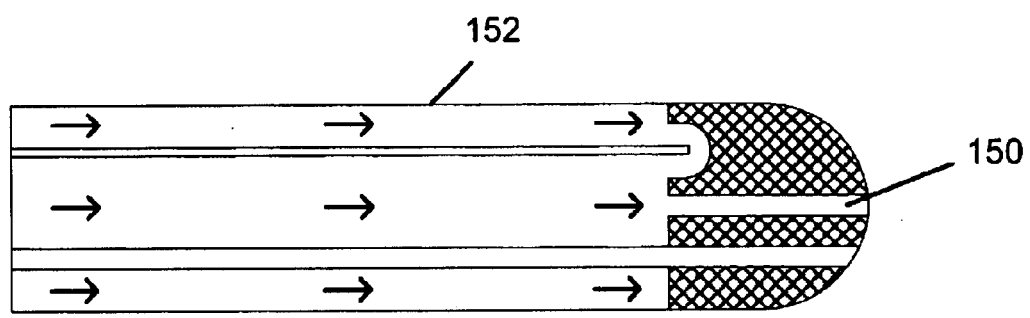
FIG. 12 is an optically heated device with a distal port.

FIG. 12 shows an embodiment of the catheter where the fluid exiting the tip through a port 150 serves to cool the catheter body 152. In this device the exterior wall of the catheter forms a central lumen which may be filled with a cooling solution. In general this volume may be too large to use for contrast injection. The fluid pressure in this sheath could also be reversed to create a vacuum on the occlusive material and remove it from the body during ablation.

Figure 13:
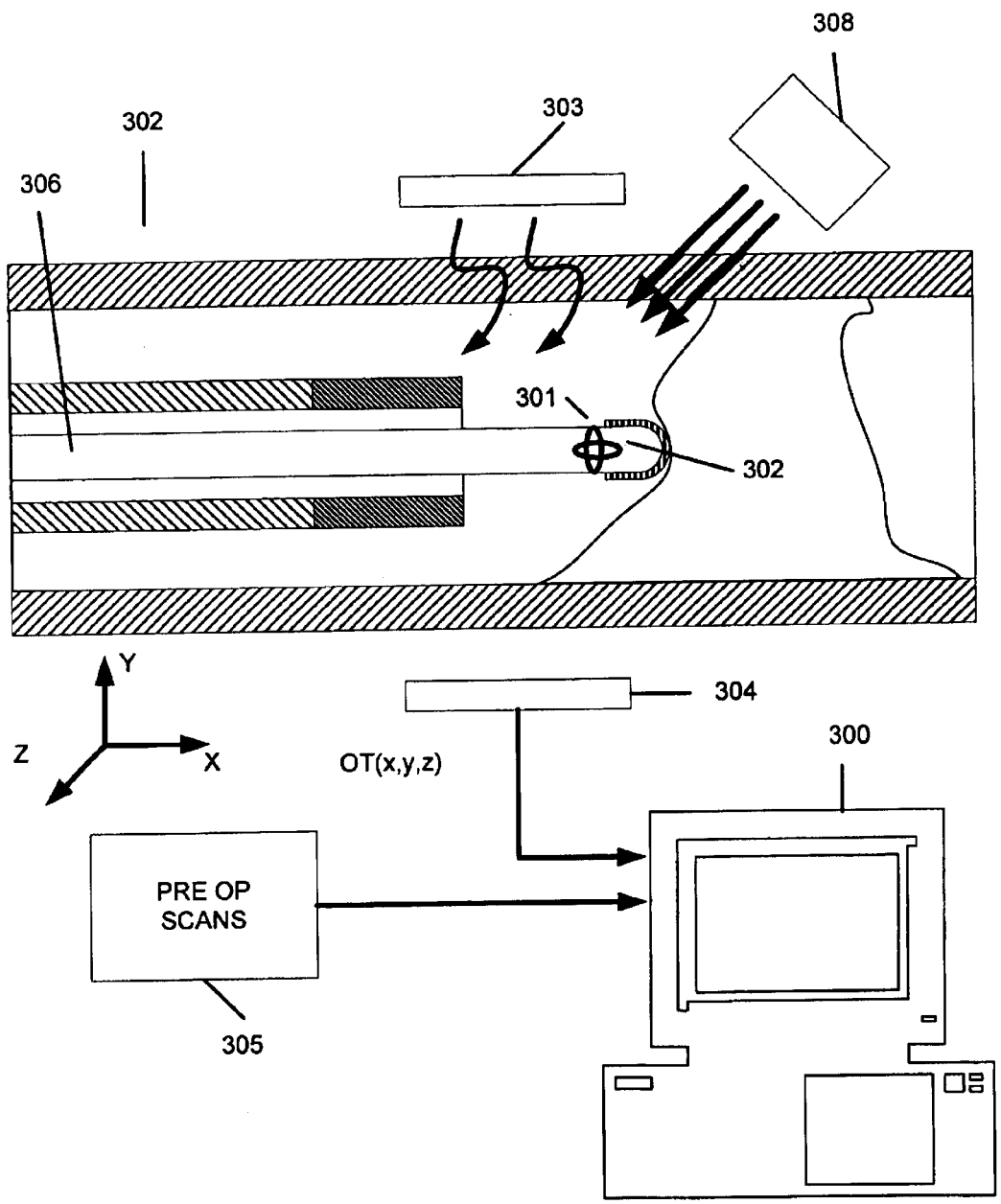
FIG. 13 is a schematic overview of the automated workstation.

FIG. 13 is a schematic diagram of a MSS system for using the catheters in a patient. In operation the physician user interacts with the patient 302 and the workstation console 300. The software used by the workstation coordinates several separate sources of data and control certain hardware as well. For example information from a preoperative scan 305 is loaded into the workstation 300 to provide a template of the treatment site. This preoperative data may be collected from MRI, CT, ultrasound, or other diagnostic imaging scans. Real time biplane x-ray data is supplied from an x-ray machine 303 and 304 to the workstation as well for display against the template and for interaction with the physician. As an alternative orthogonal coils 301 and 302 may be used with an RF location system to localize the position of the catheter.

In general a fiducial marker on the catheter allows the preoperative scan and the real time scans to be appropriately merged. In operation the user can define a location on the MSS workstation 300 with a mouse or other pointing device which identifies the desired location of the therapy. Next the MSS workstation computes the forces and required fields and gradients required to navigate the catheter to the new location. This information controls the magnet system 308.

An appropriate set of catheter actuators 306 may be provided to allow the MSS to move the catheter as well.

What is claimed is:

1. A catheter for treating an occluded vessel comprising:
   a catheter body having a proximal end and a distal end, said distal end terminating in a distal tip;
   an energy source coupled to said distal tip for supplying energy to the distal tip for treating an occlusion;
   a magnetically active element located proximate said distal tip responsive to externally applied magnetic fields whereby said externally applied magnetic fields direct and orient said distal tip.

2. The catheter of claim 1 wherein said magnetically active element forms at least a portion of said distal tip.

3. The catheter of claim 1 further including a lumen positioned in said catheter body extending form said proximal end to said distal end.

4. The catheter of claim 3 further including a laser imaging device located in said lumen for observing an occlusion.

5. The catheter of claim 3 further including a ultrasonic imaging device located in said lumen for observing an occlusion.

6. The catheter of claim 1 further including one or more electrical coils located proximate said distal tip for cooperation with a localization device.

7. A sheath for use with a catheter of claim 1 for treating a vessel occlusion comprising:
   a sheath body having a proximal end and having a distal end;
   a lumen extending from said proximal end to said distal end;
   a magnetically active element located proximate said distal tip.

8. The catheter of claim 1 including a first metallic element located proximate said distal tip adapted for coupling to a remote radio frequency energy source whereby RF energy coupled to said metallic element heats said metallic element.

9. The catheter of claim 8 wherein said metallic element forms one pole of a monopolar energy distribution system.

10. The catheter of claim 9 further comprising a second metallic element proximate said distal tip forming a pole of a bipolar energy distribution system.

11. The catheter of claim 1 including a thermally conductive element located proximate said distal tip adapted for coupling to a remote optical laser energy source whereby optical energy coupled to said thermally conductive element heats said thermally conductive element.

12. The catheter of claim 11 wherein said thermally conductive element is metallic.

13. The catheter of claim 1 further including an ultrasonic waveguide element located proximate said distal tip adapted for coupling to a remote ultrasonic frequency energy source.

14. The catheter of claim 1 further including a resistance heating element located proximate said distal tip adapted for coupling to a remote electrical energy source.

15. The catheter of claim 14 further including a resisitence heating element located proximate said distal tip adapted for coupling to a remote AC electrical energy source.

16. The catheter of claim 14 further including a resisitence heating element located proximate said distal tip adapted for coupling to a remote DC electrical energy source.

17. The catheter of claim 1 further including a fluid directing element located proximate said distal tip adapted for coupling to a remote hydraulic energy source, whereby fluid coupled to said device extracts occlusive material from locations near the distal tip.

18. A system for treating a vessel occlusion comprising:
   a sheath, having a sheath body, said sheath body having a proximal end and having a distal end;
   a lumen extending through said sheath body from said proximal end to said distal end;
   a catheter having a catheter body having a proximal end and a distal end terminating in distal tip;
   an energy source coupled to said distal tip;
   a magnetically active element located proximate said distal tip of said catheter body, responsive to externally applied magnetic fields whereby said externally applied fields direct and orient said distal tip.

19. A system for treating a vessel occlusion comprising:
   a sheath, having a sheath body, said sheath body having a proximal end and having a distal end;
   a lumen extending through said sheath body from said proximal end to said distal end;
   a catheter having a catheter body having a proximal end and a distal end;
   an energy source coupled to said distal tip for delivering therapeutic energy to a vessel occlusion;
   a magnetically active element forming a portion of said distal tip of said sheath body, responsive to externally applied magnetic fields whereby said externally applied fields direct and orient said distal tip.

20. A system for treating total occlusions of a patient's vasculature comprising:
   a catheter having an elongate body and a distal tip;
   a heated element located proximate the distal tip of the catheter;
   a magnetic element located proximate the distal tip, responsive to externally applied magnetic fields whereby said externally applied fields direct and orient said distal tip;
   a magnetic surgery system for interacting with said magnetic element;
   said magnetic surgery system including a localization device to determine the location of the catheter distal tip within the body;
   said magnetic surgery system including an occlusion visualization device for presenting an image to a user which depicts the location of the catheter tip.

21. The system of claim 20 wherein said visualization device is an ultrasonic imaging wire.

22. The system of claim 20 wherein said visualization device is a laser imaging wire.

23. A system for treating total occlusions of a patient's vasculature comprising:
   a catheter having an elongate body and a distal tip;
   a heating element located proximate the distal tip of the catheter;
   a magnetic element located proximate the distal tip, responsive to externally applied magnetic fields whereby said externally applied fields direct and orient said distal tip;
   a magnetic surgery system for interacting with said magnetic element;
   said magnetic surgery system including a localization device to determine the location of the catheter distal tip within the body;
   said magnetic surgery system including a catheter location visualization device for presenting an image to a user which depicts the location of the catheter tip.

24. The system of claim 23 wherein said catheter location visualization device is a preoperative CT image.

25. The system of claim 23 wherein said catheter location visualization device is a preoperative MRI image.

26. A method of treating a total vascular occlusion comprising the steps of:
   inserting a catheter having a magnetic tip into the body;
   directing the catheter to the location of the total occlusion;
   imaging the catheter tip to confirm and direct therapy;
   energizing said catheter to heat said distal tip;
   manipulating said distal tip by the application of external magnetic fields, directing said catheter tip into said occlusion.

* * * * *